US010478394B2

(12) United States Patent
Yu

(10) Patent No.: US 10,478,394 B2
(45) Date of Patent: Nov. 19, 2019

(54) COMPOSITIONS AND METHODS TO PROMOTE WOUND HEALING

(71) Applicant: WAYNE STATE UNIVERSITY, Detroit, MI (US)

(72) Inventor: Fu-Shin X. Yu, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/557,407

(22) PCT Filed: Mar. 10, 2016

(86) PCT No.: PCT/US2016/021847
§ 371 (c)(1),
(2) Date: Sep. 11, 2017

(87) PCT Pub. No.: WO2016/145237
PCT Pub. Date: Sep. 15, 2016

(65) Prior Publication Data
US 2018/0110726 A1    Apr. 26, 2018

Related U.S. Application Data
(60) Provisional application No. 62/131,615, filed on Mar. 11, 2015.

(51) Int. Cl.
| | | |
|---|---|---|
| *C07K 14/545* | (2006.01) | |
| *A61K 38/18* | (2006.01) | |
| *A61P 17/02* | (2006.01) | |
| *A61K 9/06* | (2006.01) | |
| *A61K 9/00* | (2006.01) | |
| *A61K 38/17* | (2006.01) | |
| *A61P 27/02* | (2006.01) | |
| *A61P 25/00* | (2006.01) | |
| *A61K 47/02* | (2006.01) | |
| *A61K 47/38* | (2006.01) | |
| *A61L 15/18* | (2006.01) | |
| *A61L 15/28* | (2006.01) | |
| *A61L 15/44* | (2006.01) | |
| *A61L 15/60* | (2006.01) | |
| *A61L 26/00* | (2006.01) | |

(52) U.S. Cl.
CPC .......... *A61K 9/0014* (2013.01); *A61K 9/0019* (2013.01); *A61K 9/06* (2013.01); *A61K 38/1793* (2013.01); *A61K 38/1858* (2013.01); *A61K 47/02* (2013.01); *A61K 47/38* (2013.01); *A61L 15/18* (2013.01); *A61L 15/28* (2013.01); *A61L 15/44* (2013.01); *A61L 15/60* (2013.01); *A61L 26/008* (2013.01); *A61L 26/0066* (2013.01); *A61P 17/02* (2018.01); *A61P 25/00* (2018.01); *A61P 27/02* (2018.01); *C07K 14/545* (2013.01); *A61L 2300/414* (2013.01); *A61L 2300/426* (2013.01); *A61L 2300/432* (2013.01); *A61L 2300/436* (2013.01); *A61L 2430/32* (2013.01); *A61L 2430/34* (2013.01)

(58) Field of Classification Search
None
See application file for complete search history.

(56) References Cited

U.S. PATENT DOCUMENTS

| | | |
|---|---|---|
| 4,618,491 A | 10/1986 | Kanematu et al. |
| 5,075,222 A | 12/1991 | Hannum et al. |
| 6,599,873 B1 | 7/2003 | Sommer et al. |
| 6,858,409 B1 | 2/2005 | Thompson et al. |
| 8,303,945 B2 | 11/2012 | Dahlen et al. |
| 8,323,635 B2 | 12/2012 | Han et al. |
| 8,563,521 B2 | 10/2013 | Skerra et al. |
| 2009/0220450 A1* | 9/2009 | Green ................ A61K 31/711 424/85.2 |

OTHER PUBLICATIONS

Escobar-Chavez, et al., "Applications of Thermo-Reversible Pluronic F-127 Gels in Pharmaceutical Formulations," J. Pharm. Science, vol. 9, No. 3, 2006, pp. 339-358.
Invitation to Pay Additional Fees dated May 27, 2016 for International Application No. PCT/US2016/021847.
Latz, et al., "Activation and Regulation of the Inflammasomes," Nat. Rev. Immunol., vol. 13, No. 6, 2013, 31 pages.
Search Report and Written Opinion dated Aug. 12, 2016 for International Application No. PCT/US2016/021847.
Thomay, et al., "Disruption of Interleukin-1 Signaling Improves the Quality of Wound Healing," The American Journal of Pathology, vol. 174, No. 6, 2009, pp. 2129-2136.
International Preliminary Report on Patentability for International Patent Application No. PCT/US2016/021847, 11 pages.

\* cited by examiner

*Primary Examiner* — Vanessa L. Ford
*Assistant Examiner* — Sandra E Dillahunt
(74) *Attorney, Agent, or Firm* — Lee & Hayes, P.C.; C. Rachal Winger; Tanya Harding

(57) ABSTRACT

The present disclosure describes compositions and methods to promote wound healing. The compositions and methods include an interleukin-1 beta (IL-1B) receptor antagonist (IL-1Ra), such as anakinra.

7 Claims, No Drawings
Specification includes a Sequence Listing.

COMPOSITIONS AND METHODS TO PROMOTE WOUND HEALING

CROSS-REFERENCE TO RELATED APPLICATION

This application is the U.S. national phase of International Patent Application No. PCT/US2016/021847, filed on Mar. 10, 2016, which claims the benefit of U.S. Provisional Application No. 62/131,615 filed on Mar. 11, 2015, the entire contents of which are incorporated by reference herein.

STATEMENT OF GOVERNMENT INTEREST

This invention was made in part using funds from United States federal grant number R01 EY010869 from the National Institutes of Health. Therefore, the United States government has certain rights in the invention.

FIELD OF THE DISCLOSURE

The present disclosure describes compositions and methods to promote wound healing. The compositions and methods utilize an interleukin-1 beta (IL-1β) receptor antagonist (IL-1Ra). In various embodiments, the compositions and methods can be used to promote wound healing, such as chronic wounds in diabetic subjects.

BACKGROUND OF THE DISCLOSURE

Two percent of the general population in the United States (U.S.) has slow or non-healing wounds (i.e., chronic wounds). Chronic wounds allow longer time for the development of infections and can contribute to the formation of bed sores and ulcers.

A common comorbid condition with chronic wounds is diabetes mellitus (diabetes). One of the most debilitating complications of chronic wounds in diabetics is the development of chronic foot ulcers. Chronic foot ulcers can necessitate limb amputation, with 50,000-60,000 performed on diabetic patients in the U.S. each year.

Another area where chronic wounds in diabetics create an acute problem is in nursing homes where diabetics are at higher risk of getting bed sores and pressure ulcers. It is estimated that 60,000 patients die each year as a direct result of a pressure ulcer.

Many diabetics also suffer from diabetic neuropathies, a type of nerve damage most often observed in the legs and feet. Patients with diabetes may have peripheral vascular disease (PVD), which usually coexists with neuropathy. When this occurs feet are described as neuroischaemic. Recently the incidence of neuroischaemic ulceration has become predominant in diabetic foot clinics and also complicates wound healing.

Depending on the affected nerves, symptoms of diabetic neuropathy can range from pain and numbness in extremities to problems with the digestive system, urinary tract, blood vessels, and heart. For some people, these symptoms are mild; for others, diabetic neuropathy can be painful, disabling, and even fatal.

SUMMARY OF THE DISCLOSURE

The present disclosure describes compositions and methods to promote wound healing. In particular embodiments, the compositions and methods are used to promote wound healing in chronic wounds. In particular embodiments, the compositions and methods are used to promote wound healing in diabetic subjects. In particular embodiments, the compositions and methods are used to promote wound healing of chronic wounds in diabetic subjects. In particular embodiments, the compositions and methods promote wound healing by promoting re-epithelialization.

The compositions and methods promote wound healing by down-regulating the activity of the pro-inflammatory cytokine, interleukin-1beta (IL-1β) at wound sites. In particular embodiments, the compositions and methods down-regulate the activity of IL-1β at wound sites where its activity is not sufficiently modulated by an IL-1β activity down-regulator, such as interleukin-1 receptor antagonist (IL-1Ra).

The IL-1Ra used in the compositions and methods disclosed herein can be anakinra and can be formulated for topical administration.

DETAILED DESCRIPTION

Slow or non-healing wounds (i.e., chronic wounds) allow longer time for the development of infections and can contribute to the formation of bed sores and ulcers. Diabetics often experience slow or limited wound healing. One of the most debilitating complications of diabetes is the development of chronic foot ulcers, which can lead to limb amputation. Additionally, diabetics may suffer from diabetic neuropathy, a type of nerve damage that can occur in people with diabetes. High blood sugar can injure nerve fibers throughout the body, but diabetic neuropathy most often damages nerves in the legs and feet.

The present disclosure describes compositions and methods to promote wound healing. In particular embodiments, the compositions and methods are used to promote wound healing in chronic wounds. In particular embodiments, the compositions and methods are used to promote wound healing in diabetic subjects. In particular embodiments, the compositions and methods are used to promote wound healing of chronic wounds in diabetic subjects.

Wound healing generally can be divided into three steps: re-epithelialization, granulation, and neovascularization. Delayed re-epithelialization and inadequate formation of granulation tissue can lead to the development of chronic wounds. Endothelial progenitor cells (EPCs), which derive from bone marrow, normally travel to sites of injury and are essential for the formation of blood vessels and wound healing. Without being bound by theory, it is believed in diabetic patients that EPCs are not properly recruited to wound sites so healing is significantly impaired.

Additionally, chronic inflammation is a hallmark of chronic wounds generally and in diabetics particularly. Inflammation and its appropriate resolution are moderated in part by a class of molecules called interleukins (e.g., signaling molecules between leukoyctes). Interleukin-1 (IL-1) is a class of proteins produced by numerous cell-types, including monocytes and some macrophages. The interleukin-1 class includes at least two 17-18 kilodalton proteins known as IL-1α and IL-1β. These proteins have important physiological effects on a number of different target cells involved in the inflammatory and immune responses. The proteins are co-mitogens (with phytohemaglutinin) for T-cells, cause both fibroblasts and chondrocytes to secrete latent collagenase, and increase the surface adhesive powers of endothelial cells for neutrophils. In addition, they act on the hypothalamus as pyrogens, they stimulate the catabolism of muscle protein, and they cause hepatocytes to synthesize a class of proteins known as "acute phase reactants."

IL-1 receptor antagonist (IL-1Ra) is an antagonist to IL-1β that is up-regulated to counteract the actions of IL-1β. It has been found that IL-1Ra is up-regulated during the healing process of normal wounds, but is not up-regulated in chronic wounds. More particularly, it has been found that IL-1Ra is up-regulated in healing corneal epithelial cells in healthy, non-diabetic mice and rats, but not in diabetic mice and rats. Further, in diabetic animals, wound healing is delayed. Without being bound by theory, increased chronic inflammation caused by unchecked IL-1β results in delayed epithelialization and inadequate granulation in the tissues of diabetic patients, leading to chronic wounds and a number of associated complications (e.g., ulcerations, sores, infections).

The present disclosure relates to compositions and methods to promote wound healing. Without being bound by theory, it is believed that the compositions and methods described herein promote wound healing by promoting re-epithelialization.

A "wound" refers to open wounds, such as incisions, lacerations, abrasions, avulsions, puncture wounds, penetration wounds, gunshot wounds, burn wounds, thermal burns, chemical burns, electrical burns, and radiation burns. "Chronic wounds" include wounds that take longer to heal than would be expected as compared to a wound of a healthy control subject. For example, a corneal incision wound is expected to heal within 42 hours following its occurrence, but in diabetic subjects, the wound becomes chronic, failing to heal within this time frame. In human subjects, a skin laceration is similarly expected to knit closed within 48 hours (if significant emergency care is not required), but would be considered chronic if it had not healed within this time frame.

In other embodiments, the compositions and methods reduce the negative effects of diabetic neuropathies. Without being bound by theory, the compositions and methods described herein can reduce chronic inflammation and promote wound healing, thereby protecting nerves from damage and enhance nerve regeneration.

In various embodiments, the compositions and methods described herein down-regulate IL-1β. In various embodiments, the compositions and methods described herein up-regulate an IL-1β antagonist. In specific embodiments, the compositions and methods up-regulate IL-1Ra.

"Up-regulated" or "Up-regulation" means increasing the presence or activity of a protein and/or increasing the expression of its gene. "Its gene" in reference to a particular protein refers to a nucleic acid sequence (used interchangeably with polynucleotide or nucleotide sequence) that encodes the particular protein. This definition also includes various sequence polymorphisms, mutations, and/or sequence variants wherein such alterations do not substantially affect the identity or function of the particular protein. Identity or function is not substantially affected if the encoded protein shares at least 90-99% sequence identity with the particular protein (sequence identity defined elsewhere) or there is no statistically significant difference in activity between the particular protein as measured by binding studies or relevant activity assays.

The presence or activity of a protein can be up-regulated by one or more of: administering the protein as a composition; increasing the expression of the protein; administering or expressing a more active variant of the protein, reducing degradation of the protein following expression, etc. To cause an up-regulation through increased expression of a protein, the copy number of its gene or genes encoding the protein may be increased. Alternatively, a strong and/or inducible promoter may be used to direct the expression of the gene, the gene being expressed either as a transient expression vehicle, or homologously or heterologously incorporated into a genome. In another embodiment, the promoter, regulatory region, and/or the ribosome binding site upstream of the gene can be altered to achieve over-expression. The expression may also be enhanced by increasing the relative half-life of the messenger or other forms of RNA. Similar mechanisms can be used to up-regulate the expression of genes, for example, genes encoding IL-1Ra.

"Down-regulated" or "down-regulation" means a decrease in the presence or activity of a protein and/or decreasing the expression of its gene. A decrease in presence or activity can be caused by: elimination of the protein's activity, blockage of the protein's activity (through, for example, a competitive receptor-binding molecule); translation of an incomplete protein sequence; incorrect folding of the protein; reduced transcription of its gene; incomplete transcription of its gene, interference with its encoded RNA transcript, or any other activity resulting in reduced presence, expression or activity of the protein.

A gene may be down-regulated for example by insertion of a foreign set of base pairs in a coding region, deletion of any portion of the gene, or by the presence of antisense sequences that interfere with transcription or translation of the gene. In another embodiment, down-regulation includes elimination of a gene's expression (i.e. gene knockout). In another embodiment, the disruption can occur by optionally inserting a nucleotide or polynucleotide molecule into the native gene sequence whereby the expression of the mutated gene is down-regulated (either partially or completely).

As is understood by one of ordinary skill in the art, "up-regulation" or "down-regulation" can be measured against a relevant control condition. For example, an up-regulation of IL-1ra can be measured by comparing an IL-1ra level to that observed in a chronic wound area of a diabetic subject. An up-regulation of IL-1ra can also be evidenced by a decrease in IL-1β's activity at a site of interest, such as a healing wound. THERAPEUTIC PROTEINS "Therapeutic proteins" include proteins that cause IL-1β to be down-regulated, such as through the up-regulation of an IL-1β antagonist. Exemplary IL-1β antagonists include IL-1Ras as described herein, such as Anakinra, marketed as Kineret® (Amgen, Inc., Thousand Oaks, Calif., USA), and the exemplary therapeutic protein sequences found in Table 1, as well as variants, d-substituted analogs, and modifications thereof. Additional therapeutic proteins can be found in U.S. Pat. Nos. 6,858,409; 6,599,873; 5,075,222; 8,323,635; and 8,303,945. Therapeutic proteins can be synthetic or naturally-occurring. Sequence information provided by public databases can be used to identify gene sequences encoding proteins disclosed herein and vice versa.

TABLE 1

Exemplary Therapeutic Proteins and Representative Encoding Sequence

| SEQ ID NO. | Sequence |
|---|---|

1  (X1)(X2)PSGRKSSKMQAFRIWDVNQKTFYLRNNQLVAGYLQGPNVNLEEKI
   DVVPIEPHALFLGIHGGKMCLSCVKSGDETRLQLEAVNITDLSENRKQDKRF
   AFIRSDSGPTTSFESAACPGWFLCTAMEADQPVSLTNMPDEGVMVTKFYF
   QEDE
   wherein (X$_1$) is M or nothing and (X$_2$) is R or P.

2  (X$_1$)RPSGRKSSKMQAFRIWDVNQKTFYLRNNQLVAGYLQGPNVNLEEKIDV
   VPIEPHALFLGIHGGKMCLSCVKSGDETRLQLEAVNITDLSENRKQDKRFAF
   IRSDSGPTTSFESAACPGWFLCTAMEADQPVSLTNMPDEGVMVTKFYFQE
   DE
   wherein (X$_1$) is M or nothing.

3  MEICRGLRSHLITLLLFLFHSETIC(X$_1$)(X$_2$)PSGRKSSKMQAFRIWDVNQKTF
   YLRNNQLVAGYLQGPNVNLEEKIDVVPIEPHALFLGIHGGKMCLSCVKSGD
   ETRLQLEAVNITDLSENRKQDKRFAFIRSDSGPTTSFESAACPGWFLCTAM
   EADQPVSLTNMPDEGVMVTKFYFQEDE
   wherein (X$_1$) is M or nothing and (X$_2$) is R or P.

4  (X1)(X$_2$)PSGRKSSKMQAFR
   wherein (X$_1$) is M or nothing and (X$_2$) is R or P.

5  DVNQKTFYLRNNQLVAGYLQGPNVNLEEKIDVVP

6  DVNQKTFYLRNNQLVAGYLQGPNVNL

7  YLRNNQLVAGYLQGPNVNLEEKIDVVP

8  DFGVMVTKFYFQED

9  DEGVMVTKFYFQ 10 (X$_1$)RPSGRKSSKMQAFRIWDVNQKTFYLRNNQLVAGYLQGPNVNLEEKIDV
   VIEPHALFLGIHGGKMCLSCVKSGDETRLQLEAVNITDLSENRKQDKRFAFI
   RSDSGPTTSFESAACPGWFLCTAMEADQPVSLTNMPDEGVMVTKFYFQE
   DE
   wherein (X$_1$) is M or nothing 11 (X$_1$)RPSGRKSSKMQAFRIWDVNQKTFYLRNNQLVAGYLQsPNVNLEEKIDV
   VPIEPHALFLGIHGGKMCLSCVKSGDETRLQLEAVNITDLSENRKQDKRFAF
   IRSDSGPTTSFESAACPGWFLCTAMEADQPVSLTNMPDEGVMVTKFYFQE
   DE
   wherein (X$_1$) is M or nothing 12 (X$_1$)RPSGRKSSKMQAFRIWDVNQKTFYLRNNQLVAGYLQGPNVNLEEKIDV
   VPIEPHALFLGIHGGKMCLSCVKSGDETRLQLEAVNITDLSENRKQDKRFAF
   IRSDSGPTTSFESAACPGWFLCTAMEADQPVSLTNMPDECVMVTKFYQED
   E
   wherein (X$_1$) is M or nothing 13 MEICRGLRSHLITLLLFLFHSETIC(X$_1$)RPSGRKSSKMQAFRIWDVNQKTFYL
   RNNQLVAGYLQGPNVNLEEKIDVVPIEPHALFLGIHGGKMCLSCVKSGDET
   RLQLEAVNITDLSENRKQDKRFAFIRSDSGPTTSFESAACPGWFLCTAMEA
   DQPVSLTNMPDECVMVTKFYQEDE
   wherein (X$_1$) is M or nothing 14 MPPSGRKSSKMQAFRIWDVNQKTFYLRNNQLVAGYLQGPNVNLEEKIDVV
   PIEPHALFLGIHGGKMCLSCVKSGDETRLQLEAVNITDLSENRKQDKRFAFI
   RSDSGPTTSFESAACPGWFLCTAMEADQPVSLTNMPDEGVMVTKFYFQE
   DE 15 (X$_1$)(X$_2$)PSCRKSSKMQAPRIWDVNQKTFYLRNNQLVAGYLQGPNVNLEEKI
   DVVPIEPHALFLGIHGGKMCLSCVKSGDETRLQLEAVNITDLSENRKQDKRF
   AFIRSDSGPTTSFESAACPGWFLCTAMEADQPVSLTNMPDEGVMVTKFYF
   QEDE
   wherein (X$_1$) is M or nothing and (X$_2$) is R or P 16 (X$_1$)RPSGRKSSKMQAFRIWDVNQKTFYLRNNQLVAGYLQGPNVNLEEKIDV
   VPIEPHALFLGIHGGKHCLSCVKSGDETRLQLEAVNITDLSENRKQDKRFAFI
   RSDSGPTTSFESAACPGWFLCTAMEADQPVSLTNMPDEGVMVTKFYFQE
   DE
   wherein (X$_1$) is M or nothing TABLE 1-continued Exemplary Therapeutic Proteins and Representative Encoding Sequence

| SEQ ID NO. | Sequence |
|---|---|
| 17 | (X₁)(X₂)PSGRKSSKMQAFRIWDVNQKTFYLRNNQLVAGYLQGPNVNLEEKI<br>DVVPIEPHALFLGIHGGKMCLSCVKSGDETRLQLEAVNITDLSENRXQDKHF<br>AFIRSDEGPTTSFESAACPGWFLCTAMEADQPVSLTNMPDEGVMVTKFYF<br>QEDE<br>Wherein (X₁) is M or nothing and (X₂) is R or P |
| 18 | (X₁)RPSGRKSSKMQAERIWDVNQKTFYLRNNQLVAGYLQGPNVNLEEKIDV<br>VPIEPHALFLGIHGGKMCLSCVKSGDETRLQLEAVNITDLSENRKQDKRFAF<br>IRSDSGPTTSFESAACPGWFLCTAMEADQPVSLTNMPDEGVMVTKFYFQE<br>DE<br>wherein (X₁) is M or nothing. |
| 19 | (X₁)RPSGRKSSKMQAFRIWDVNQKTFYLRNNQLVAGYLQGPNVNLEEKIDV<br>VPTEPHALFLGIHGGKMCLSCVKSGDETRLQLEAVNITDLSENRKQDKRFA<br>FIRSDSGPTTSFESAACPGWFLCTAMEADQPVSLTNMPDEGVMVTKFYFQ<br>EDE<br>wherein (X₁) is M or nothing |
| 20 | (X₁)RPSGRKSSKMQAFRIWDVNQKTFYLRNNQLVAGYLQGPNVNLEEKIDV<br>VPIEPHALFLGIHGGKMCLSCVKSGDETRLQLEAVNITDLSENRKQDKRFAF<br>IPSDSGPTTSFESAACPGWFLCTAMEADQPVSLTNMPDEGVMVTKFYFQE<br>DE<br>wherein (X₁) is M or nothing |
| 21 | M(X₁)PSGRKSSKMQAFRIWDVNQKTFYLRNNQLVAGYLQGPNVNLEEKIDV<br>VPIEPHALFLGIHGGKMCLSCVKSGDETRLQLEAVNITDLSENRKQDKRFAF<br>IRSDSGPTTSFESAACPGWFLCTAMEADQPVSLTNMPDEGVMVTKFYFQE<br>DE<br>wherein (X₁) is R or P |
| 22 | (X₁)RPSGRKSSKMQAFRIWDVNQKTFYLRNNQLVAGYLQGPNVNLEEKIDV<br>VPIEPHALFLGIHGGKMCLSCVKSGDETRLQLEAVNITDLSENRXQDKRFAF<br>IRSDSGPTTSFESAACPGWFLCTAMEADQPVSLTNMPDEGVMVTKFYFQE<br>DE<br>wherein (X₁) is M or nothing |
| 23 | (X1)(X2)(X3)PSG(X4)RK(X5)S(X6)SKMQAFRIWDVNQKTFYLRNNQLVAGY<br>LQGPNVNLEEKIDVVPIEPHALFLGIFIGGKMCLSCVKSGDETRLQLEA(X7)V<br>NITDLSENRKQDKRFAFIRSDSGPTTSFESAA(X8)PGWFLCTAMEADQPVS<br>LTNMPDE(X9)GVMVTKFYFQEDE<br>wherein: (X1) is C or nothing (X2) is M or nothing, (X3) is R or P, (X4)-(X7) is<br>a C or nothing, (X8) is C or S, and (X9) is C or nothing. |
| 24 | MEICRGLRSHLITLLLFLFHSETICRPSGRKSSKMQAFRIWDVNQKTFYLRN<br>NQLVAGYLQGPNVNLEEKIDVVPIEPHALFLGIHGGKMCLSCVKSGDETRL<br>QLEAVNITDLSENRKQDKRFAFIRSDSGPTTSFESAACPGWFLCTAMEADQ<br>PVSLTNMPDEGVMVTKFYFQEDE |
| 25 | MRPSGKRPCKMQAFRIWDTNQKTFYLRNNQLIAGYLQGPNIKLEEKIDMVPI<br>DLHSVFLGIHGGKLCLSCAKSGDDIKLQLEEVNITDLSKNKEEDKRFTFIRSE<br>KGPTTSFESAACPGWFLCTTLEADRPVSLTNTPEEPLIVTKFYFQEDQ |
| 26 | MRPSGRKSSKMQAFRIWDVNQKTFYLRNNQLVAGYLQGPNVNLEEKIDVV<br>PIEPHALFLGIHGGKMCLSCVKSGDETRLQLEAVNITDLSENRKQDKRFAFI<br>RSDSGPTTSFESAACPGWFLCTAMEADQPVSLTNMPDEGVMVTKFYFQE<br>DE |
| 27 | ggaagacctcctgtcctatcaggccctcccatggctttagagacgatctgccgaccctctgggagaaaat<br>ccagcaagatgcaagccttcagaatctgggatgttaaccagaagaccttctatctgaggaacaaccaact<br>agttgccggatacttgcaaggaccaaatgtcaatttagaagaaaagatagatgtggtacccattgagcctc<br>atgctctgttcttgggaatccatggagggaagatgtgcctgtcctgtcaagtctggtgatgagaccagact<br>ccagctggaggcagttaacatcactgacctgagcgagaacagaaagcaggacaagcgcttcgccttcat<br>ccgctcagacagtggcccaccaccagttttgagtctgccgcctgcccggttggttcctctgcacagcgat<br>ggaagctgaccagcccgtcagcctcaccaatatgcctgacgaaggcgtcatggtcaccaaattctacttcc<br>aggaggacgagtagtactgcccaggcctgcctgttcccattcttgcatggcaaggactgcagggactgcc<br>agtcccctgccccagggctcccggctatgggggcactgaggaccagccattgagggggtggaccctcag<br>aaggcgtcacaacaacctggtcacaggactctgcctcctcttcaactgaccagcctccatgctgcctccag<br>aatggtctttctaatgtgtgaatcagagcacagcagccctgcacaaagcccttccatgtcgcctctgcattc<br>aggatcaaacccgaccacctgcccaacctgctctcctcttgccactgcctcttcctccctcattccaccttcc<br>catgccctggatccatcaggccacttgatgaccccccaaccaagtggctcccacaccctgttttacaaaaaa<br>gaaaagaccagtccatgagggaggttttttaagggttttgtggaaaatgaaaattaggatttcatgattttttttttt<br>cagtcccccgtgaaggagagcccttcatttggagattatgttctttcggggagaggctgaggacttaaaatatt<br>cctgcatttgtgaaatgatggtgaaagtaagtggtagcttttcccttctttttcttcttttttttgtgatgtcccaacttgt<br>aaaaaattaaaagttatggtactatgttagccccataattttttttttttccttttaaaacacttccataatctggactcct |

TABLE 1-continued

Exemplary Therapeutic Proteins and Representative Encoding Sequence

SEQ
ID
NO. Sequence

```
ctgtccaggcactgctgcccagcctccaagctccatctccactccagatttttttacagctgcctgcagtacttta
cctcctatcagaagtttctcagctcccaaggctctgagcaaatgtggctcctgggggttctttcttcctctgctga
aggaataaattgctccttgacattgtagagcttctggcacttggagacttgtatgaaagatggctgtgcctctg
cctgtctcccccaccaggctgggagctctgcagagcaggaaacatgactcgtatatgtctcaggtccctgc
agggccaagcacctagcctcgctcttggcaggtactcagcgaatgaatgctgtatatgttgggtgcaaagtt
ccctacttcctgtgacttcagctctgttttacaataaaatcttgaaaatgcctaaaaaaaaaaaaaaaaaaa
aaaaaaaaaaaaaaaaaaaaaaaaaaaaaaaaaaaa
```

"Variants" include therapeutic proteins having one or more amino acid additions, deletions, stop positions, or substitutions, as compared to a therapeutic protein disclosed elsewhere herein.

An amino acid substitution can be a conservative or a non-conservative substitution. Variants of therapeutic proteins disclosed herein can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other groups including amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of therapeutic proteins disclosed herein also include proteins with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a therapeutic protein sequence disclosed herein.

Variants of therapeutic proteins disclosed herein include proteins that share: 70% sequence identity with any of SEQ ID NO:1-26; 75% sequence identity with any of SEQ ID NO: 1-26; 80% sequence identity with any of SEQ ID NO: 1-26; 81% sequence identity with any of SEQ ID NO: 1-26; 82% sequence identity with any of SEQ ID NO1-26; 83% sequence identity with any of SEQ ID NO: 1-26; 84% sequence identity with any of SEQ ID NO: 1-26; 85% sequence identity with any of SEQ ID NO: 1-26; 86% sequence identity with any of SEQ ID NO: 1-26; 87% sequence identity with any of SEQ ID NO: 1-26; 88% sequence identity with any of SEQ ID NO: 1-26; 89% sequence identity with any of SEQ ID NO: 1-26; 90% sequence identity with any of SEQ ID NO: 1-26; 91% sequence identity with any of SEQ ID NO: 1-26; 92% sequence identity with any of SEQ ID NO: 1-26; 93% sequence identity with any of SEQ ID NO: 1-26; 94% sequence identity with any of SEQ ID NO: 1-26; 95% sequence identity with any of SEQ ID NO: 1-26; 96% sequence identity with any of SEQ ID NO: 1-26; 97% sequence identity with any of SEQ ID NO: 1-26; 98% sequence identity with any of SEQ ID NO: 1-26; or 99% sequence identity with any of SEQ ID NO: 1-26.

Particular exemplary embodiments include therapeutic proteins wherein the proteins share 80% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity with SEQ ID NO:24.

"% sequence identity" refers to a relationship between two or more sequences, as determined by comparing the sequences. In the art, "identity" also means the degree of sequence relatedness between protein sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNAS- TAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" mean any set of values or parameters which originally load with the software when first initialized.

"D-substituted analogs" include therapeutic proteins disclosed herein having one more L-amino acids substituted with D-amino acids. The D-amino acid can be the same amino acid type as that found in the protein sequence or can be a different amino acid. Accordingly, D-substituted analogs are also variants.

"Modifications" include therapeutic proteins disclosed herein, wherein one or more amino acids have been replaced with a non-amino acid component, or where the amino acid has been conjugated to a functional group or a functional group has been otherwise associated with an amino acid or protein. The modified amino acid may be, e.g., a glycosylated amino acid, a PEGylated amino acid, a farnesylated amino acid, an acetylated amino acid, a biotinylated amino acid, an amino acid conjugated to a lipid moiety, an amino acid conjugated to human serum albumin, or an amino acid conjugated to an organic derivatizing agent. The presence of modified amino acids may be advantageous in, for example, (a) increasing functional in vivo half-life, (b) reducing protein antigenicity, (c) increasing protein storage stability, (d) increasing protein solubility, and/or (e) increasing bioavailability, e.g. increasing the area under the curve (AUCsc). Amino acid(s) can be modified, for example, co-translationally or post-translationally during recombinant production (e.g., N-linked glycosylation at N—X-S/T motifs during expression in mammalian cells) or modified by synthetic means. The modified amino acid can be within the sequence or at the terminal end of a sequence.

Polynucleotide sequences encoding the disclosed proteins (in addition to SEQ ID NO: 27) can be readily deduced by one of ordinary skill in the art.

Compositions

Compositions can be formed by combining a therapeutic protein, or a pharmaceutically acceptable prodrug thereof, with a pharmaceutically acceptable carrier suitable for delivery to a subject in accordance with known methods of drug delivery.

Prodrugs of therapeutic proteins, such as IL-1Ra (e.g., SEQ ID NO:1-26 and particularly SEQ ID NO: 24) refer to a protein that can undergo biotransformation (e.g., either spontaneous or enzymatic) within a subject to release, or to convert to, (e.g., enzymatically, mechanically, electromagnetically, etc.) an active or more active form of the protein. Prodrugs can be used to overcome issues associated with stability, toxicity, lack of specificity, or limited bioavailability. Exemplary prodrugs include a therapeutic protein and a chemical masking group (e.g., a group that reversibly suppresses the activity of the protein). Some preferred prodrugs are variants or modifications of therapeutic proteins that have sequences that are cleavable under metabolic conditions. Exemplary prodrugs become active or more active in vivo or in vitro when they undergo a biochemical transformation (e.g., phosphorylation, hydrogenation, dehydrogenation, glycosylation, etc.). Prodrugs often offer advantages of solubility, tissue compatibility, or delayed release (See e.g., Bundgard, Design of Prodrugs, pp. 7-9, 21-24, Elsevier, Amsterdam (1985); and Silverman, The Organic Chemistry of Drug Design and Drag Action, pp. 352-401, Academic Press, San Diego, Calif. (1992)).

In some embodiments, the pharmaceutical compositions can include, for example, 25 µg/mL-5 mg/mL, 50 µg/mL-5 mg/mL, 100 µg/mL-5 mg/mL, 150 µg/mL-5 mg/mL, 200 µg/mL-5 mg/mL, 250 µg/mL-5 mg/mL, 300 µg/mL-5 mg/mL, 350 µg/mL-5 mg/mL, 400 µg/mL-5 mg/mL, 450 µg/mL-5 mg/mL, 500 µg/mL-5 mg/mL, 550 µg/mL-5 mg/mL, 600 µg/mL-5 mg/mL, 650 µg/mL-5 mg/mL, 700 µg/mL-5 mg/mL, 750 µg/mL-5 mg/mL, 800 µg/mL-5 mg/mL, 850 µg/mL-5 mg/mL, 900 µg/mL-5 mg/mL, 950 µg/mL-5 mg/mL, 1 mg/mL-5 mg/mL, 1.5 mg/mL-5 mg/mL, 2 mg/mL-5 mg/mL, 2.5 mg/mL-5 mg/mL, 3 mg/mL-5 mg/mL, 3.5 mg/mL-5 mg/mL, 4 mg/mL-5 mg/mL, 4.5 mg/mL-5 mg/mL, 25 µg/mL-2.5 mg/mL, 50 µg/mL-2.5 mg/mL, 100 µg/mL-2.5 mg/mL, 150 µg/mL-2.5 mg/mL, 200 µg/mL-2.5 mg/mL, 250 µg/mL-2.5 mg/mL, 300 µg/mL-2.5 mg/mL, 350 µg/mL-2.5 mg/mL, 400 µg/mL-2.5 mg/mL, 450 µg/mL-2.5 mg/mL, 500 µg/mL-2.5 mg/mL, 550 µg/mL-2.5 mg/mL, 600 µg/mL-2.5 mg/mL, 650 µg/mL-2.5 mg/mL, 700 µg/mL-2.5 mg/mL, 750 µg/mL-2.5 mg/mL, 800 µg/mL-2.5 mg/mL, 850 µg/mL-2.5 mg/mL, 900 µg/mL-2.5 mg/mL, 950 µg/mL-2.5 mg/mL, 1 mg/mL-2.5 mg/mL, 1.5 mg/mL-2.5 mg/mL, 2 mg/mL-2.5 mg/mL, 25 µg/mL-1 mg/mL, 50 µg/mL-1 mg/mL, 100 µg/mL-1 mg/mL, 150 µg/mL-1 mg/mL, 200 µg/mL-1 mg/mL, 250 µg/mL-1 mg/mL, 300 µg/mL-1 mg/mL, 350 µg/mL-1 mg/mL, 400 µg/mL-1 mg/mL, 450 µg/mL-1 mg/mL, 500 µg/mL-1 mg/mL, 550 µg/mL-1 mg/mL, 600 µg/mL-1 mg/mL, 650 µg/mL-1 mg/mL, 700 µg/mL-1 mg/mL, 750 µg/mL-1 mg/mL, 800 µg/mL-1 mg/mL, 850 µg/mL-1 mg/mL, 900 µg/mL-1 mg/mL, 950 µg/mL-1 mg/mL, 25 µg/mL-750 µg/mL, 50 µg/mL-750 µg/mL, 100 µg/mL-750 µg/mL, 150 µg/mL-750 µg/mL, 200 µg/mL-750 µg/mL, 250 µg/mL-750 µg/mL, 300 µg/mL-750 µg/mL, 350 µg/mL-750 µg/mL, 400 µg/mL-750 µg/mL, 450 µg/mL-750 µg/mL, 500 µg/mL-750 µg/mL, 550 µg/mL-750 µg/mL, 600 µg/mL-750 µg/mL L, 650 µg/mL-750 µg/mL, 700 µg/mL-750 µg/mL, 25 µg/mL-500 µg/mL, 50 µg/mL-500 µg/mL, 100 µg/mL-500 µg/mL, 150 µg/mL-500 µg/mL, 200 µg/mL-500 µg/mL, 250 µg/mL-500 µg/mL, 300 µg/mL-500 µg/mL, 350 µg/mL-500 µg/mL, 400 µg/mL-500 µg/mL, 450 µg/mL-500 µg/mL, 25 µg/mL-250 µg/mL, 50 µg/mL-250 µg/mL, 100 µg/mL-250 µg/mL, 150 µg/mL-250 µg/mL, 200 µg/mL-250 µg/mL, 25 µg/mL-100 µg/mL, or 50 µg/mL-100 µg/mL of the therapeutic protein.

In particular embodiments, the compositions disclosed herein can be formulated for topical administration. The compositions disclosed herein can also be formulated for intradermal, intralesional, intraocular, intravaginal, intrarectal, intramuscular, and/or subcutaneous administration.

In particular embodiments, the compositions can be in the form of, e.g., gels, ointments, pastes, lotions, creams, sprays, foams, or powders.

A gel is a substantially dilute cross-linked system, which exhibits no flow when in the steady-state. Most gels are liquid, however they behave more like solids due to the three-dimensional cross-linked network within the liquid. Gels can have properties ranging from soft and weak to hard and tough.

An ointment is a homogeneous, viscous, semi-solid preparation, most commonly a greasy, thick oil (oil 80%- water 20%) with a high viscosity. Ointments have a water number, which is the maximum quantity of water that 100 g of a base can contain at 20° C.

A paste includes three agents—oil, water, and powder, one of which includes a therapeutic agent. Pastes can be an ointment in which a powder is suspended.

A lotion also includes oil, water, and powder, but can have additional components (e.g., alcohol to hold the emulsion together) and often has a lower viscosity than a paste.

A cream is an emulsion of oil and water in approximately equal proportions. Creams are thicker than lotions and maintain their shape when removed from a container.

Topical formulations disclosed herein can include components, such as animal and vegetable fats, oils, waxes, paraffins, starch, tragacanth, cellulose derivatives, polyethylene glycols, silicones, bentonites, silicic acid, talc and zinc oxide, or mixtures thereof. In various embodiments, topical formulations may include thickening agents, surfactants, organic solvents, tonicity modifiers, In various embodiments, topical formulations can be prepared using thickening agents, such as carboxymethylcellulose sodium, sodium starch glycollate type C, or Carbomers such as Carbopol® (Lubrizol Advanced Materials, Inc. Cleveland, Ohio, USA) 934, 980, 981, 1382, 5984, or 2984. In various embodiments, topical formulations can be prepared using surfactants, such as Pluronic® (BASF Corporation, Mount Olive, N.J., USA) co-polymers, such as Pluronic® F-127, and/or a Pluronic® co-polymer having the formula H(OCH2CH2)$_x$

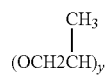

(OCH2CH2)$_z$ OH (wherein x is 2 to 130, y is 15 to 70, and z is 2 to 130), or H[OCH2CH2]$_{49}$[OCHCH2]$_{67}$ [OCH2CH2]$_{49}$OH; propyl glycol, polypropylene glycol (PPG) stearyl ethers, such as PPG ethers of stearyl alcohol including PPG-20 methyl glucose ether distearate, PPG-15 Stearyl Ether, and PPG-11 Stearyl Ether.

In various embodiments, topical formulations such as gel formulations may include an organic solvent (e.g. a lower alkyl alcohol, such as ethyl alcohol or isopropyl alcohol; a ketone, such as acetone or N-methyl pyrrolidone; a glycol, such as propylene glycol; and the like, or mixtures thereof) present in an amount of 1% to 99%. In particular embodiments, an organic solvent may be present in an amount of 60% to 80%. In various embodiments, topical formulations may include a cellulose derivative, such as hydroxyl ethyl cellulose, hydroxy propyl cellulose, hydroxy propyl methyl cellulose, methyl cellulose, carboxy methyl cellulose, sodium carboxy methyl cellulose, ethyl cellulose, and the like, or combinations thereof present in an amount of 0.1% to 20%. In particular embodiments a cellulose derivative may be present in an amount of 0.5% to 5%.

In various embodiments, topical formulations such as gel formulations include any suitable tonicity modifier. Exemplary suitable tonicity modifiers include sodium chloride, potassium chloride, mannitol, sucrose, lactose, fructose, maltose, dextrose, dextrose anhydrous, propylene glycol, and glycerol. In various embodiments, the tonicity modifier can be present in an amount of 0.5% to 1% by weight. In particular embodiments, a tonicity modifier can be present in an amount of 0.8% to about 1% by weight of the topical formulation. In various embodiments, buffers can be present in the topical formulations. Exemplary buffers include phosphate buffered saline (PBS) acetate buffers, such as sodium acetate trihydrate or glacial acetic acid; and citrate buffers, such as sodium citrate dihydrate and citric acid.

In some embodiments, topical formulations such as gel formulations may have a viscosity of at least 1,000 centipoise (cps). In other embodiments, topical formulations such as gel formulations may have a viscosity of at least about 3,000 cps. In specific embodiments, the viscosity of topical formulations will not exceed 50,000 cps.

Powders and sprays particularly may benefit from the inclusion of excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane. The compositions of the disclosure can be alternatively administered by aerosol. This is accomplished by preparing an aqueous aerosol, liposomal preparation, or solid particles containing a composition of the disclosure. A non-aqueous (e.g., fluorocarbon propellant) suspension also could be used. Sonic nebulizers can be preferred because they minimize exposing the compositions to shear, which can result in degradation of the composition.

Compositions can also be incorporated into wound dressings (e.g., bandages, adhesive bandages, transdermal patches). Generally, in these embodiments, compositions are embedded within puffs, gauzes, fleeces, gels, powders, sponges, or other materials that are associated with a second layer to form a wound dressing. Absorption enhancers can also be used to increase the flux of the composition, and particularly the therapeutic protein within the composition, across the skin. The rate of such flux can be controlled by either providing a rate controlling membrane or dispersing the therapeutic protein in a polymer matrix or gel.

In particular embodiments, the second layer of a wound dressing can be an elastomeric layer, vapor-permeable film, waterproof film, a woven or nonwoven fabric, mesh, or the like. The composition containing layer and second layer can be bonded using any suitable method (e.g., the application of adhesives, such as pressure sensitive adhesives, hot melt adhesives, curable adhesives; the application of heat or pressure, such as in lamination; a physical attachment through the use of stitching, studs, other fasteners; or the like).

Wound dressings may include adhesives for attachment to the skin or other tissue. Although any adhesive suitable for forming a bond with the skin or other tissue can be used, in certain embodiments a pressure sensitive adhesive is used. Pressure sensitive adhesives are generally defined as adhesives that adhere to a substrate when a light pressure is applied but leave little to no residue when removed. Pressure sensitive adhesives include solvent in solution adhesives, hot melt adhesives, aqueous emulsion adhesives, calenderable adhesives, and radiation curable adhesives.

The most commonly used elastomers in pressure sensitive adhesives can include natural rubbers, styrene-butadiene latexes, polyisobutylene, butyl rubbers, acrylics, and silicones. In particular embodiments, acrylic polymer or silicone-based pressure sensitive adhesives can be used. Acrylic polymers can often have a low level of allergenicity, be cleanly removable from skin, possess a low odor, and exhibit low rates of mechanical and chemical irritation. Medical grade silicone pressure sensitive adhesives can be chosen for their biocompatibility.

Amongst the factors that influence the suitability of a pressure sensitive adhesive for use in wound dressings of particular embodiments is the absence of skin irritating components, sufficient cohesive strength such that the adhesive can be cleanly removed from the skin, ability to accommodate skin movement without excessive mechanical skin irritation, and good resistance to body fluids.

In particular embodiments, the pressure sensitive adhesive can include a butyl acrylate. While butyl acrylate pressure sensitive adhesives can generally be used for many applications, any pressure sensitive adhesive suitable for bonding skin can be used. Such pressure sensitive adhesives are well known in the art.

In other embodiments, the compositions disclosed herein may be formulated for injection, including subcutaneous, subdermal, and/or intraocular. U.S. Pat. No. 7,918,824 discloses syringes suitable for subject use. The compositions for injection can take such forms as suspensions, solutions or emulsions in oily or aqueous vehicles, and can contain formulatory agents such as suspending, stabilizing, preserving and/or dispersing agents. Injectable formulations include one or more compositions disclosed herein in combination with one or more pharmaceutically acceptable sterile isotonic aqueous or non-aqueous solutions, emulsions, or sterile powders which may be reconstituted into sterile injectable solutions or dispersions just prior to use, which may contain antioxidants, buffers, bacteriostats, or solutes.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Examples of suitable aqueous and non-aqueous carriers, which may be employed in the injectable formulations include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of selected particle size in the case of dispersions, and by the use of surfactants.

Injectable formulations may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the pharmaceutical compositions.

Alternatively, the therapeutic protein can be in lyophilized and/or provided in powder form for constitution with a suitable vehicle, e.g., sterile pyrogen-free water, before use. Lyophilized compositions can include less than 5% water content; less than 4.0% water content; or less than 3.5% water content.

In another embodiment, the composition can be in a unit dosage form, such as in a suitable diluent in sterile, hermetically sealed ampoules or sterile syringes.

In some cases, in order to prolong the effect of a composition, it is desirable to slow the absorption of the composition following injection. Compositions can be formulated as sustained-release systems utilizing semipermeable matrices of solid polymers containing at least one therapeutic protein. Various sustained-release materials have been established and are well known by those of ordinary skill in the art. Sustained-release systems may, depending on their chemical nature, release active ingredients following administration for a few weeks up to over 100 days.

In various embodiments, delayed absorption can be accomplished by dissolving or suspending the composition in an oil vehicle. In various embodiments, therapeutic proteins can be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. In addition, prolonged absorption of the injectable pharmaceutical form may be brought about by the inclusion of agents which delay absorption such as aluminum monostearate and gelatin.

Injectable depot forms can be made by forming microencapsule matrices of therapeutic proteins in biodegradable polymers such as polylactide-polyglycolide. Depending on the ratio of therapeutic protein to polymer, and the nature of the particular polymer employed, the rate of therapeutic protein release can be controlled. Examples of other biodegradable polymers include poly(orthoesters) and poly(anhydrides). Injectable depot formulations are also prepared by entrapping the therapeutic protein in liposomes or microemulsions which are compatible with body tissue.

Alternatively, delayed absorption of a composition can be accomplished by the use of a liquid suspension of crystalline or amorphous material having poor water solubility. The rate of absorption of the composition then depends upon its rate of dissolution which, in turn, may depend upon crystal size and crystalline form.

Any composition disclosed herein can advantageously include any other pharmaceutically acceptable carriers which include those that do not produce significantly adverse, allergic, or other untoward reactions that outweigh the benefit of administration, whether for research, prophylactic, and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Methods of Treatment

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with therapeutic proteins disclosed herein including salts and prodrugs thereof. Treating subjects includes delivering therapeutically effective amounts. Therapeutically effective amounts include those that provide effective amounts, prophylactic treatments, and/or therapeutic treatments. Therapeutically effective amounts can be administered to promote wound healing. In particular embodiments, the promotion of wound healing leads to re-epithelialization, reduction in the occurrence and/or severity of ulcers, and/or preservation of nerve function (appropriate signal transduction) and/or integrity (physical state of the nerve).

An "effective amount" is the amount of a therapeutic protein necessary to result in a desired physiological change in the subject. Effective amounts are often administered for research purposes. Effective amounts disclosed herein promote wound healing and/or reduce, control, or eliminate the negative effects of neuropathies.

A "prophylactic treatment" includes a treatment administered to a subject who display signs or symptoms of wounds that have not yet become chronic or display only early signs or warning symptoms for the development of chronic wounds or neuropathies such that treatment is administered for the purpose of diminishing, preventing, or decreasing the risk of the wound becoming chronic or developing the chronic wounds or neuropathies further. Thus, a prophylactic treatment functions as a preventative treatment against chronic wounds or neuropathies. A prophylactic treatment also can be administered to subjects at risk for developing chronic wounds before early signs or warning appear. For example, in subjects at risk for developing chronic wounds, prophylactic treatments can be administered at the time a wound occurs or as soon as is reasonably or practically possible thereafter. Diabetic subjects are one group of subjects at risk for developing chronic wounds. Other subjects at risk for developing chronic wounds include those who suffer from an inflammatory condition.

A "therapeutic treatment" includes a treatment administered to a subject who has chronic wounds or neuropathies and is administered to the subject for the purpose of promoting the healing of the chronic wounds or neuropathies. Therapeutic treatments can promote wound healing and/or reduce, control, or eliminate the negative effects of neuropathies.

Objective measures for the promotion of wound healing include the time required for the closure of an open wound or establishment of a biological barrier. For example, diabetic subjects provided with a treatment disclosed herein will demonstrate faster wound healing than diabetic subjects with a similar wound who do not receive a treatment disclosed herein. As an additional example, treatments disclosed herein can resolve chronic wounds—e.g., result in the healing of previously chronic wounds that would not have healed, but for administration of a treatment disclosed herein.

Objective measures for re-epithelialization can include slit lamp microscopy with fluorescence staining. Objective measures for reduction and/or severity of ulcers can include slit lamp microscopy for surface (ir)regularity. Objective measures for the reduction of negative effects of neuropathies can include restoring sensitivity and measurement of sensory nerve density, thickness, and branching.

Objective measures for preservation of nerve function can include sensitivity measures. Objective measures for preservation of nerve integrity can include in vitro confocal microscopy to determine the nerve fiber health (length, diameters and branches.)

For skin neuropathy, muscle strength and tone, tendon reflexes, and sensitivity to touch, temperature and vibration can be measured. The measurements can include the Filament test. Sensitivity to touch may be tested using a soft nylon fiber called a monofilament. If a subject is unable to feel the filament on, for example, the feet, this is a sign of lost sensation in those nerves, Nerve conduction studies, electromyography (EMG), and quantitative sensory testing (noninvasive tests used to assess how nerves respond to vibration and changes in temperature) can also be used.

For administration, therapeutically effective amounts (also referred to herein as doses) can be initially estimated based on results from in vitro assays and/or animal model studies. For example, a dose can be formulated in animal models to achieve a circulating concentration range that includes an $IC_{50}$ as determined in cell culture against a particular target. Such information can be used to more accurately determine useful doses in subjects of interest.

The actual dose amount administered to a particular subject can be determined by a physician, veterinarian, or researcher taking into account parameters such as physical and physiological factors including target, body weight, severity of wound, type of wound, previous or concurrent therapeutic interventions, idiopathy of the subject, and route of administration.

The amount and concentration of therapeutic protein in a composition, as well as the quantity of the pharmaceutical composition administered to a subject, can be selected based on clinically relevant factors, the solubility of the therapeutic protein in the composition, the potency and activity of the therapeutic protein, and the manner of administration of the composition. A composition including a therapeutically effective amount of a therapeutic protein disclosed herein, or a pharmaceutically acceptable salt or prodrug thereof, can be administered to a subject for treatment of wounds or neuropathies in a clinically safe and effective manner, including one or more separate administrations of the composition. For example, about 0.05 mg/kg to about 5.0 mg/kg can be administered to a subject per day in one or more doses (e.g., doses of about 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID or 2.0 mg/kg BID). For certain indications, the total daily dose of a therapeutic protein can be about 0.05 mg/kg to about 3.0 mg/kg administered to a subject one to three times a day, including administration of total daily doses of about 0.05-3.0, 0.1-3.0, 0.5-3.0, 1.0-3.0, 1.5-3.0, 2.0-3.0, 2.5-3.0, and 0.5-3.0 mg/kg/day of therapeutic proteins of Table 1 using 60-minute QD, BID or TID dosing. In one particular example, pharmaceutical compositions can be administered QD or BID to a subject with, e.g., total daily doses of 1.5 mg/kg, 3.0 mg/kg, 4.0 mg/kg of a composition with up to about 92-98% wt/v.

Additional useful doses can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly.

In particular embodiments, the compositions described herein can be used in conjunction with other wound treatments. For example, in the case of a diabetic ulcer, sharp debridement, pressure relief, and various methods of infection control may be used.

In various embodiments, a topical formulation of a composition as described herein can be applied to the wound. In some embodiments, a topical formulation is applied superficially and the wound is then covered by a dressing. In particular embodiments, the dressing is moistened. In some embodiments, the dressing can be moistened by saline. In various embodiments, the dressing can be left in place for up to 6 hours, up to 12 hours, or up to 24 hours. In particular embodiments, the dressing is removed, the topical formulation is reapplied, and a new dressing is used to cover the wound.

The compositions disclosed herein can be administered with additional components to reduce the occurrence of unwanted events during wound healing. For example, the compositions described herein can be administered with therapeutics for the treatment of diabetic ulcers such as Becaplermin (e.g., Regranex® (Smith & Nephew, Inc., Memphis, Tenn., USA)).

In various embodiments, the compositions described herein can be administered with antiplatelet medications (e.g. irreversible cyclooxygenase inhibitors, adenosine diphosphate (ADP) receptor inhibitors, phosphodiesterase inhibitors, protease-activated receptor-1 (PAR-1) antagonists, glycoprotein IIB/IIIA inhibitors, adenosine reuptake inhibitors, or thromboxane inhibitors), growth factors (e.g. platelet-derived growth factor (PDGF)), and/or vasodilators.

In various embodiments, the compositions can be administered in combination with anti-inflammatory agents including nonsteroidal anti-inflammatory drugs (NSAIDs), such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and/or corticosteroids, such as cortisone, hydrocortisone, methylprednisolone, prednisone, prednisolone, betamethasone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

The compositions can also be administered with anti-infective agents including anthelmintics (e.g., mebendazole), antibiotics including aminoclycosides (e.g., gentamicin, neomycin, tobramycin), antifungal antibiotics (e.g., amphotericin b, fluconazole, griseofulvin, itraconazole, ketoconazole, nystatin, micatin, tolnaftate), cephalosporins (e.g., cefaclor, cefazolin, cefotaxime, ceftazidime, ceftriaxone, cefuroxime, cephalexin), betalactam antibiotics (e.g., cefotetan, meropenem), chloramphenicol, macrolides (e.g., azithromycin, clarithromycin, erythromycin), penicillins (e.g., penicillin G sodium salt, amoxicillin, ampicillin, dicloxacillin, nafcillin, piperacillin, ticarcillin), tetracyclines (e.g., doxycycline, minocycline, tetracycline), bacitracin, clindamycin, colistimethate sodium, polymyxin b sulfate, vancomycin, antivirals (e.g., acyclovir, amantadine, didanosine, efavirenz, foscarnet, ganciclovir, indinavir, lamivudine, nelfinavir, ritonavir, saquinavir, stavudine, valacyclovir, valganciclovir, and zidovudine), quinolones (e.g., ciprofloxacin, levofloxacin), sulfonamides (e.g., sulfadiazine, sulfisoxazole), sulfones (e.g., dapsone), furazolidone, metronidazole, pentamidine, sulfanilamidum crystallinum, gatifloxacin, and sulfamethoxazole/trimethoprim.

Compositions can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

The described formulations can deliver relevant compositions directly or can administer genetic therapies to up- or down-regulate a target. A desired gene can be introduced intracellularly and incorporated within subject cellular DNA for expression, by homologous recombination (Koller and Smithies, 1989, Proc. Natl. Acad. Sci. USA 86:8932-8935; Zijlstra et al., 1989, Nature 342:435-438). In particular embodiments, the desired gene recombinantly expressed in the subject includes an inducible promoter operably linked to the coding region, such that expression of the recombinant gene is controllable by controlling the presence or absence of the appropriate inducer of transcription.

Genetic therapies can be achieved using any method known in the art, including transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, sheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present disclosure.

In particular embodiments retroviral vectors can be used (Miller et al., 1993, Meth. Enzymol. 217:581-599; Boesen et al., 1994, Biotherapy 6:291-302, Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114) adenoviruses can be used (Kozarsky and Wilson, 1993, Current Opinion in Genetics and Development 3:499-503, Rosenfeld et al., 1991, Science 252:431-434; Rosenfeld et al., 1992, Cell 68:143-155; and Mastrangeli et al., 1993, J. Clin. Invest. 91:225-234), Adena-associated viruses, mammalian artificial chromosomes (Vos, 1998, Curr. Op. Genet. Dev. 8:351-359; liposomes (Tarahovsky and Ivanitsky, 1998, Biochemistry (Mose) 63:607-618); ribozymes (Branch and Klotman, 1998, Exp. Nephrol. 6:78-83); and triplex DNA can also be used (Chan and Glazer, 1997, J. Mol. Med. 75:267-282).

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Example 1

The corneal injury model was utilized in both diabetic and normal rats for 2 days. IL-1β, one of the key genes in the inflammation cascade (pro-inflammasome regulation), was elevated significantly in normal tissue (healing epithelium). This elevation generally requires an increase in IL-1Ra, which is shown in healthy (normal) tissue in the rat experiment. In diabetes, IL-1β expression is increased; however, IL1Ra is not increased or elevated. In short, the IL-1Ra is needed to check inflammation, but remains unchecked in diabetes. Inflammation is a major cause of complications in diabetic patients and can be due to a lack of IL-1Ra. Without being bound by theory, the increased chronic inflammation caused by unchecked IL-1β results in delayed epithelialization and inadequate granulation in the tissues of diabetic patients, leading to a number of complications with ulcerations and infections.

In experiments, topical application of recombinant mouse IL-1Ra accelerates epithelial wound closure in vivo both in mice and rat type 1 diabetic wound models. Topical application of recombinant mouse IL-1Ra accelerates epithelial wound closure in vivo in both mice and rat type 1 diabetic wound models.

Example 2

Pluronic® F-127 formulation: One gram of carboxymethylcellulose sodium (1%, w/w, final concentration) was dissolved in 50 ml water with constant agitation. The solution was then cooled to 5-10° C. and 25-30 g Pluronic® F-127 was added while agitating, 10 ml 10×PBS was also added, bringing the total volume to 100 ml. The gel was stored at 4° C. until a clear solution was formed, and the gel was autoclaved (120° C., 20 min). The solution is cooled to 4° C., 67 µl anakinra injection solution (100 mg in 0.67 mL, or 150 mg/ml) will be added to 10 ml solution and stored at 4° C. all the time giving 100 µg/ml. Preventives can be used.

Regranex and Anakinra, Regranex 10 ml may be mixed with 6.7 µl anakinra injection solution to yield 100 µg/ml Anakinra.

Example 3

Subjects with diabetes mellitus (DM) often develop corneal complications and delayed wound healing.

Animals and Induction of Diabetes. All investigations will conform to the regulations of the ARVO Statement for the Use of Animals in Ophthalmic and Vision Research, the National Institutes of Health.

Streptozotocin (STZ) induction of type 1 DM in Sprague-Dawley (SD) rats. Male Sprague-Dawley (SD) rats will be purchased. These rats will be divided into two groups. Half will undergo induction of type I DM with an intraperitoneal injection of 55 mg/kg of streptozotocin in ice-cold 0.01 M citrate buffer (pH 4.5), with the controls will be injected with citrate buffer alone. A second dose of STZ will be injected after 4 to 5 days in animals with serum glucose levels less than 200 mg/dL. This regimen will produce insulin-deficient DM in 100% of the animals. The animals injected with citrate buffer will be normoglycemic. Type 2 Goto-Kakizaki (GK) rats will be maintained under standard conditions. C57BL/6 mice will be induced to develop type 1 DM according a Low-Dose STZ Induction Protocol (mouse). Particularly, for mice, 50 mg/kg will be injected constitutively for 5 days.

Glucose levels and body weight will be monitored weekly. Animals with blood sugar levels higher than 400 mg/dL (STZ-SD rats), 220 mg/dL (GK), and 350 mg/dL (STD-mice) will be considered diabetic and will be used, with age-matched animals as the control, at 8 weeks post STZ treatment for SD rats, 6 months old for GK rats and 10 week post STZ for mice. These are times when epithelial wound closure is significantly delayed and many pathologies can be observed in DM animals.

Corneal Epithelial Debridement Wound. Anesthetized rats and mice will be first demarcated with a trephine in the central cornea (5-mm circular wound for rats and 2 mm for mice). Bacitracin ophthalmic ointment will be applied to the cornea after surgery to prevent infection. At 42 hours (rats) or 24 hours (mice) post wounding (hours post wounding: "hpw"), the same size trephine will be used to mark the original wound.

Subconjunctival Injection of IL-1Ra Polypeptides. For mice, 5 µl of IL-1Ra solution will be injected into the subconjunctival space at 1 site at the superior part of the cornea and for rats, 20 µl at 2 sites, 10 µl each at the superior and inferior quadrants. IL-1Ra will be injected 4-6 hours and/or 24 hours prior to wounding.

Results will show that IL-1Ra will accelerate delayed epithelial wound closure in DM corneas.

The Experiment will be repeated with various IL-1Ra (e.g. Anakinra) and Regranex combination therapies. The combination therapies results will show acceleration of delayed epithelial wound closure in DM corneas.

Example 4

A number of experiments are conducted to further define the role of up-regulation of IL-1Ra (e.g., Anakinra, SEQ ID NOs. 1-26) and the beneficial combination of IL-1Ra with a platelet-derived growth factor (e.g., Regranex) to promote wound healing, promote re-epithelialization, reduce the occurrence and/or severity of ulcers, preserve nerve function and/or integrity, and promote eye health and/or maintenance of vision. In the experiments, each experiment having relevant control conditions, each of the listed compounds is administered as part of a composition (including as a direct therapeutic and/or as part of a genetic therapy as described herein). The experiments assess the function of IL-1Ra as an IL-1 (both IL-1α, and more importantly, IL-1β) neutralizer to suppress inflammation and inflammation caused tissue damage. Particular experiments will follow a procedure described elsewhere herein and/or can include use of the following animal models of chronic wounds: rabbit ear ischemia; pig flap ischemia; rat magnet ischemia reperfusion and/or pig wound infection. With the objective end points for each treatment outcome, the compositions are shown to cause significantly significant improvements as follows:

| Compound | Treatment Outcome | Objective End Point |
| --- | --- | --- |
| Anakinra | Promotes wound healing | Time to wound closure or establishment of a biological barrier |
| | Promotes re-epithelialization | Establishment of a biological barrier or Superficial Punctate Keratitis (death of small groups of cells on the surface of the cornea that can be examined by a slit lamp) |
| | Reduces occurrence and/or severity of ulcers | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | Visual scores as determined by an ophthalmologist |

-continued

| Compound | Treatment Outcome | Objective End Point |
|---|---|---|
| Anakinra formulated for topical administration | Promotes wound healing | Time to wound closure or establishment of a biological barrier |
| | Promotes re-epithelialization | Establishment of a biological barrier or Superficial Punctate Keratitis |
| | Reduces occurrence and/or severity of ulcers | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | Visual scores as determined by an ophthalmologist |
| Anakinra formulated as a gel | Promotes wound healing | Time to wound closure or establishment of a biological barrier |
| | Promotes re-epithelialization | Establishment of a biological barrier or Superficial Punctate Keratitis |
| | Reduces occurrence and/or severity of ulcers | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | clear and transparent cornea, no fluorescence staining under a slit lamp microscope |
| Anakinra in combination with Regranex | Promotes wound healing | Time to wound closure or establishment of a biological barrier |
| | Promotes re-epithelialization | Establishment of a biological barrier or Superficial Punctate Keratitis |
| | Reduces occurrence and/or severity of ulcers | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | Visual scores as determined by an ophthalmologist |
| SEQ ID NO: 1, 2, 3, 4, 5, 6, 7, 8, 9, 10, 11, 12, 13, 14, 15, 16, 17, 18, 19, 20, 21, 22, 23, 24, 25 and 26 | Promotes wound healing | Time to wound closure or establishment of a biological barrier |
| | Promotes re-epithelialization | Establishment of a biological barrier or Superficial Punctate Keratitis |
| | Reduces occurrence and/or severity of ulcers | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | Visual scores as determined by an ophthalmologist |
| SEQ ID NO: 1, 2, 3, 4, 5, 6, 7, 8, 9, 10, 11, 12, 13, 14, 15, 16, 17, 18, 19, 20, 21, 22, 23, 24, 25 and 26 formulated for topical administration and/or in combination with Regranex | Promotes wound healing | Time to wound closure or establishment of a biological barrier |
| | Promotes re-epithelialization | Establishment of a biological barrier or Superficial Punctate Keratitis |
| | Reduces occurrence and/or severity of ulcers | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | Visual scores as determined by an ophthalmologist |
| SEQ ID NO: 27 | Promotes wound healing | Time to wound closure or establishment of a biological barrier |
| | Promotes re-epithelialization | Establishment of a biological barrier or Superficial Punctate Keratitis |
| | Reduces occurrence and/or severity of ulcers, | Slit lamp microscopy for surface (ir)regularity |
| | Preserves nerve function integrity | Corneal (or skin) sensitivity. |
| | Preserves nerve integrity | Confocal microscopy to determine the nerve fiber health (length, diameters and branches) |
| | Promotes eye health | Epithelial integrity, ocular surface regularity and/or normal tear secretion. |
| | Maintains vision | Visual scores as determined by an ophthalmologist |

The tested compounds will also suppress inflammation by neutralizing IL-1β activity.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in an embodiment's ability to promote wound healing in a chronic wound of a diabetic subject.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with any drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of promoting healing of a chronic wound in a diabetic subject comprising administering to the chronic wound a therapeutically effective amount of a gel comprising a therapeutic agent consisting of a therapeutic protein consisting of the sequence provided in SEQ ID NO: 26 (anakinra), thereby promoting healing of the chronic wound.

2. The method of claim 1, wherein the chronic wound is a diabetic ulcer.

3. The method of claim 1, wherein the administering is topically administering.

4. The method of claim 1, further comprising applying a wound dressing to the wound.

5. The method of claim 4, wherein the administering and applying are achieved in one step.

6. The method of claim 4, wherein the wound dressing is an adhesive bandage.

7. The method of claim 1 further comprising administering a platelet-derived growth factor and/or Becaplermin.

* * * * *

SEQUENCE LISTING

<160> NUMBER OF SEQ ID NOS: 27

<210> SEQ ID NO 1
<211> LENGTH: 153
<212> TYPE: PRT
<213> ORGANISM: Artificial Sequence

```
<220> FEATURE:
<223> OTHER INFORMATION: Modifications of Chain A, Initial
      Crystallographic Analyses Of A Recombinant Interleukin-1 Receptor
      Antagonist Protein or Chain A, Solution Structure Of Human
      Interleukin-1 Receptor Antagonist Protein
<220> FEATURE:
<221> NAME/KEY: (X1) = Xaa
<222> LOCATION: (1)..(1)
<223> OTHER INFORMATION: (X1) is Met or nothing
<220> FEATURE:
<221> NAME/KEY: (X2) = Xaa
<222> LOCATION: (2)..(2)
<223> OTHER INFORMATION: (X2) is Arg or Pro

<400> SEQUENCE: 1

Xaa Xaa Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 2
<211> LENGTH: 153
<212> TYPE: PRT
<213> ORGANISM: Artificial Sequence
<220> FEATURE:
<223> OTHER INFORMATION: Modified Chain A, Solution Structure Of Human
      Interleukin-1 Receptor Antagonist Protein or modified Chain A,
      Initial Crystallographic Analyses Of A Recombinant Interleukin-1
      Receptor Antagonist Protein
<220> FEATURE:
<221> NAME/KEY: (X1) = Xaa
<222> LOCATION: (1)..(1)
<223> OTHER INFORMATION: (X1) = Xaa is Met or nothing.

<400> SEQUENCE: 2

Xaa Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
```

```
                        85                  90                  95
Lys Arg Phe Ala Phe Ile Arg Ser Asp Ser Gly Pro Thr Thr Ser Phe
                100                 105                 110

Glu Ser Ala Ala Cys Pro Gly Trp Phe Leu Cys Thr Ala Met Glu Ala
            115                 120                 125

Asp Gln Pro Val Ser Leu Thr Asn Met Pro Asp Glu Gly Val Met Val
        130                 135                 140

Thr Lys Phe Tyr Phe Gln Glu Asp Glu
145                 150

<210> SEQ ID NO 3
<211> LENGTH: 178
<212> TYPE: PRT
<213> ORGANISM: Artificial Sequence
<220> FEATURE:
<223> OTHER INFORMATION: Modifications of interleukin-1 receptor
      antagonist protein isoform 1 precursor
<220> FEATURE:
<221> NAME/KEY: (X1)= Xaa
<222> LOCATION: (26)..(26)
<223> OTHER INFORMATION: (X1)  is Met or nothing
<220> FEATURE:
<221> NAME/KEY: (X2)= Xaa
<222> LOCATION: (27)..(27)
<223> OTHER INFORMATION: (X2) is Arg or Pro

<400> SEQUENCE: 3

Met Glu Ile Cys Arg Gly Leu Arg Ser His Leu Ile Thr Leu Leu Leu
1               5                   10                  15

Phe Leu Phe His Ser Glu Thr Ile Cys Xaa Xaa Pro Ser Gly Arg Lys
            20                  25                  30

Ser Ser Lys Met Gln Ala Phe Arg Ile Trp Asp Val Asn Gln Lys Thr
        35                  40                  45

Phe Tyr Leu Arg Asn Asn Gln Leu Val Ala Gly Tyr Leu Gln Gly Pro
    50                  55                  60

Asn Val Asn Leu Glu Glu Lys Ile Asp Val Val Pro Ile Glu Pro His
65                  70                  75                  80

Ala Leu Phe Leu Gly Ile His Gly Gly Lys Met Cys Leu Ser Cys Val
                85                  90                  95

Lys Ser Gly Asp Glu Thr Arg Leu Gln Leu Glu Ala Val Asn Ile Thr
            100                 105                 110

Asp Leu Ser Glu Asn Arg Lys Gln Asp Lys Arg Phe Ala Phe Ile Arg
        115                 120                 125

Ser Asp Ser Gly Pro Thr Thr Ser Phe Glu Ser Ala Ala Cys Pro Gly
    130                 135                 140

Trp Phe Leu Cys Thr Ala Met Glu Ala Asp Gln Pro Val Ser Leu Thr
145                 150                 155                 160

Asn Met Pro Asp Glu Gly Val Met Val Thr Lys Phe Tyr Phe Gln Glu
                165                 170                 175

Asp Glu

<210> SEQ ID NO 4
<211> LENGTH: 15
<212> TYPE: PRT
<213> ORGANISM: Artificial Sequence
<220> FEATURE:
<223> OTHER INFORMATION: Modifications of amino acids 1-15 of Human
      Interleukin-1 Receptor Antagonist Protein
<220> FEATURE:
<221> NAME/KEY: (X1)= Xaa
<222> LOCATION: (1)..(1)
```

```
<223> OTHER INFORMATION: (X1) is Met or nothing
<220> FEATURE:
<221> NAME/KEY: (X2)= Xaa
<222> LOCATION: (2)..(2)
<223> OTHER INFORMATION: (X2) is Arg or Pro

<400> SEQUENCE: 4

Xaa Xaa Pro Ser Gly Arg Lys Ser Ser Lys Met Gln Ala Phe Arg
1               5                   10                  15

<210> SEQ ID NO 5
<211> LENGTH: 34
<212> TYPE: PRT
<213> ORGANISM: Artificial Sequence
<220> FEATURE:
<223> OTHER INFORMATION: Amino acids 18-51 of Chain A, Solution
      Structure Of Human Interleukin-1 Receptor Antagonist Protein

<400> SEQUENCE: 5

Asp Val Asn Gln Lys Thr Phe Tyr Leu Arg Asn Asn Gln Leu Val Ala
1               5                   10                  15

Gly Tyr Leu Gln Gly Pro Asn Val Asn Leu Glu Glu Lys Ile Asp Val
            20                  25                  30

Val Pro

<210> SEQ ID NO 6
<211> LENGTH: 26
<212> TYPE: PRT
<213> ORGANISM: Artificial Sequence
<220> FEATURE:
<223> OTHER INFORMATION: Amino acids 18-43  of Chain A, Solution
      Structure Of Human Interleukin-1 Receptor Antagonist Protein

<400> SEQUENCE: 6

Asp Val Asn Gln Lys Thr Phe Tyr Leu Arg Asn Asn Gln Leu Val Ala
1               5                   10                  15

Gly Tyr Leu Gln Gly Pro Asn Val Asn Leu
            20                  25

<210> SEQ ID NO 7
<211> LENGTH: 27
<212> TYPE: PRT
<213> ORGANISM: Artificial Sequence
<220> FEATURE:
<223> OTHER INFORMATION: Amino acids 25-51  of Chain A, Solution
      Structure Of Human Interleukin-1 Receptor Antagonist Protein

<400> SEQUENCE: 7

Tyr Leu Arg Asn Asn Gln Leu Val Ala Gly Tyr Leu Gln Gly Pro Asn
1               5                   10                  15

Val Asn Leu Glu Glu Lys Ile Asp Val Val Pro
            20                  25

<210> SEQ ID NO 8
<211> LENGTH: 14
<212> TYPE: PRT
<213> ORGANISM: Artificial Sequence
<220> FEATURE:
<223> OTHER INFORMATION: Modifications of either Amino acids 163-176 of
      interleukin-1 receptor antagonist protein isoform 1 precursor;
      Amino acids 145-158 of interleukin-1 receptor antagonist protein
      isoform 3; or Amino acids 166-179 of interleukin-1 receptor
      antagonist

<400> SEQUENCE: 8

Asp Phe Gly Val Met Val Thr Lys Phe Tyr Phe Gln Glu Asp
```

<210> SEQ ID NO 9
<211> LENGTH: 12
<212> TYPE: PRT
<213> ORGANISM: Artificial Sequence
<220> FEATURE:
<223> OTHER INFORMATION: Modifications of Amino acids 163-176, 166-179, 145-158 or 126-142 of interleukin-1 receptor antagonist protein isoform 1, 2, 3, and 4 precursors, respectively

<400> SEQUENCE: 9

Asp Glu Gly Val Met Val Thr Lys Phe Tyr Phe Gln
1               5                   10

<210> SEQ ID NO 10
<211> LENGTH: 152
<212> TYPE: PRT
<213> ORGANISM: Artificial Sequence
<220> FEATURE:
<223> OTHER INFORMATION: Modifications Chain A, Solution Structure Of Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing

<400> SEQUENCE: 10

Xaa Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
                20                  25                  30

Ala Gly Tyr Leu Gln Gly Pro Asn Val Asn Leu Glu Glu Lys Ile Asp
            35                  40                  45

Val Val Ile Glu Pro His Ala Leu Phe Leu Gly Ile His Gly Gly Lys
        50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 11
<211> LENGTH: 153
<212> TYPE: PRT
<213> ORGANISM: Artificial Sequence
<220> FEATURE:
<223> OTHER INFORMATION: Modification of Chain A, Solution Structure Of Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing

<400> SEQUENCE: 11

Xaa Arg Pro Ser Gly Arg Lys Ser Ser Lys Met Gln Ala Phe Arg Ile
1               5                   10                  15

```
Trp Asp Val Asn Gln Lys Thr Phe Tyr Leu Arg Asn Asn Gln Leu Val
            20                  25                  30

Ala Gly Tyr Leu Gln Ser Pro Asn Val Asn Leu Glu Glu Lys Ile Asp
        35                  40                  45

Val Val Pro Ile Glu Pro His Ala Leu Phe Leu Gly Ile His Gly Gly
 50                  55                  60

Lys Met Cys Leu Ser Cys Val Lys Ser Gly Asp Glu Thr Arg Leu Gln
 65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 12
<211> LENGTH: 152
<212> TYPE: PRT
<213> ORGANISM: Artificial Sequence
<220> FEATURE:
<223> OTHER INFORMATION: Modifications of Chain A, Initial
      Crystallographic Analyses Of A Recombinant Interleukin-1 Receptor
      Antagonist Protein or Chain A, Solution Structure Of Human
      Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing

<400> SEQUENCE: 12

Xaa Arg Pro Ser Gly Arg Lys Ser Ser Lys Met Gln Ala Phe Arg Ile
 1               5                  10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
 50                  55                  60

Lys Met Cys Leu Ser Cys Val Lys Ser Gly Asp Glu Thr Arg Leu Gln
 65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Cys Val Met Val
    130                 135                 140

Thr Lys Phe Tyr Phe Gln Glu Asp Glu
145                 150

<210> SEQ ID NO 13
<211> LENGTH: 177
<212> TYPE: PRT
```

<213> ORGANISM: Artificial Sequence
<220> FEATURE:
<223> OTHER INFORMATION: Modified interleukin-1 receptor antagonist
      protein isoform 1 precursor [homo sapiens]
<220> FEATURE:
<221> NAME/KEY: (X1)= Xaa
<222> LOCATION: (26)..(26)
<223> OTHER INFORMATION: (X1) is Met or nothing

<400> SEQUENCE: 13

Met Glu Ile Cys Arg Gly Leu Arg Ser His Leu Ile Thr Leu Leu Leu
1               5                   10                  15

Phe Leu Phe His Ser Glu Thr Ile Cys Xaa Arg Pro Ser Gly Arg Lys
            20                  25                  30

Ser Ser Lys Met Gln Ala Phe Arg Ile Trp Asp Val Asn Gln Lys Thr
        35                  40                  45

Phe Tyr Leu Arg Asn Asn Gln Leu Val Ala Gly Tyr Leu Gln Gly Pro
50                  55                  60

Asn Val Asn Leu Glu Glu Lys Ile Asp Val Val Pro Ile Glu Pro His
65                  70                  75                  80

Ala Leu Phe Leu Gly Ile His Gly Gly Lys Met Cys Leu Ser Cys Val
                85                  90                  95

Lys Ser Gly Asp Glu Thr Arg Leu Gln Leu Glu Ala Val Asn Ile Thr
            100                 105                 110

Asp Leu Ser Glu Asn Arg Lys Gln Asp Lys Arg Phe Ala Phe Ile Arg
        115                 120                 125

Ser Asp Ser Gly Pro Thr Thr Ser Phe Glu Ser Ala Ala Cys Pro Gly
130                 135                 140

Trp Phe Leu Cys Thr Ala Met Glu Ala Asp Gln Pro Val Ser Leu Thr
145                 150                 155                 160

Asn Met Pro Asp Glu Cys Val Met Val Thr Lys Phe Tyr Gln Glu Asp
                165                 170                 175

Glu

<210> SEQ ID NO 14
<211> LENGTH: 153
<212> TYPE: PRT
<213> ORGANISM: Artificial Sequence
<220> FEATURE:
<223> OTHER INFORMATION: Modified Human Interleukin-1 Receptor
      Antagonist Protein

<400> SEQUENCE: 14

Met Pro Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala

-continued

```
                115                 120                 125
Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 15
<211> LENGTH: 153
<212> TYPE: PRT
<213> ORGANISM: Artificial Sequence
<220> FEATURE:
<223> OTHER INFORMATION: Modifications of either Chain A, Initial
      Crystallographic Analyses Of A Recombinant Interleukin-1 Receptor
      Antagonist Protein or Chain A, Solution Structure Of Human
      Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing
<220> FEATURE:
<221> NAME/KEY: (X2)= Xaa
<222> LOCATION: (2)..(2)
<223> OTHER INFORMATION: (X2) is Arg or Pro

<400> SEQUENCE: 15

Xaa Xaa Pro Ser Cys Arg Lys Ser Ser Lys Met Gln Ala Pro Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 16
<211> LENGTH: 153
<212> TYPE: PRT
<213> ORGANISM: Artificial Sequence
<220> FEATURE:
<223> OTHER INFORMATION: Modifications of Chain A, Solution Structure Of
      Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing

<400> SEQUENCE: 16

Xaa Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30
```

```
Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
 50                  55                  60

Lys His Cys Leu Ser Cys Val Lys Ser Gly Asp Glu Thr Arg Leu Gln
 65                  70                  75                  80

Leu Glu Ala Val Asn Ile Thr Asp Leu Ser Glu Asn Arg Lys Gln Asp
                 85                  90                  95

Lys Arg Phe Ala Phe Ile Arg Ser Asp Ser Gly Pro Thr Thr Ser Phe
                100                 105                 110

Glu Ser Ala Ala Cys Pro Gly Trp Phe Leu Cys Thr Ala Met Glu Ala
                115                 120                 125

Asp Gln Pro Val Ser Leu Thr Asn Met Pro Glu Gly Val Met Val
                130                 135                 140

Thr Lys Phe Tyr Phe Gln Glu Asp Glu
145                 150

<210> SEQ ID NO 17
<211> LENGTH: 153
<212> TYPE: PRT
<213> ORGANISM: Artificial Sequence
<220> FEATURE:
<223> OTHER INFORMATION: Modifications of Chain A, Solution Structure Of
      Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing
<220> FEATURE:
<221> NAME/KEY: (X2)= Xaa
<222> LOCATION: (2)..(2)
<223> OTHER INFORMATION: (X2) is Arg or Pro
<220> FEATURE:
<221> NAME/KEY: misc_feature
<222> LOCATION: (94)..(94)
<223> OTHER INFORMATION: Xaa can be any naturally occurring amino acid

<400> SEQUENCE: 17

Xaa Xaa Pro Ser Gly Arg Lys Ser Ser Lys Met Gln Ala Phe Arg Ile
 1               5                  10                  15

Trp Asp Val Asn Gln Lys Thr Phe Tyr Leu Arg Asn Asn Gln Leu Val
                 20                  25                  30

Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
 50                  55                  60

Lys Met Cys Leu Ser Cys Val Lys Ser Gly Asp Glu Thr Arg Leu Gln
 65                  70                  75                  80

Leu Glu Ala Val Asn Ile Thr Asp Leu Ser Glu Asn Arg Xaa Gln Asp
                 85                  90                  95

Lys His Phe Ala Phe Ile Arg Ser Asp Glu Gly Pro Thr Thr Ser Phe
                100                 105                 110

Glu Ser Ala Ala Cys Pro Gly Trp Phe Leu Cys Thr Ala Met Glu Ala
                115                 120                 125

Asp Gln Pro Val Ser Leu Thr Asn Met Pro Asp Glu Gly Val Met Val
                130                 135                 140

Thr Lys Phe Tyr Phe Gln Glu Asp Glu
145                 150
```

-continued

```
<210> SEQ ID NO 18
<211> LENGTH: 153
<212> TYPE: PRT
<213> ORGANISM: Artificial Sequence
<220> FEATURE:
<223> OTHER INFORMATION: Modifications of Chain A, Solution Structure Of
      Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing.

<400> SEQUENCE: 18

Xaa Arg Pro Ser Gly Arg Lys Ser Ser Lys Met Gln Ala Glu Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 19
<211> LENGTH: 153
<212> TYPE: PRT
<213> ORGANISM: Artificial Sequence
<220> FEATURE:
<223> OTHER INFORMATION: Modificatins of Chain A, Solution Structure Of
      Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing

<400> SEQUENCE: 19

Xaa Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Thr Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110
```

-continued

```
Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 20
<211> LENGTH: 153
<212> TYPE: PRT
<213> ORGANISM: Artificial Sequence
<220> FEATURE:
<223> OTHER INFORMATION: Modifications of Chain A, Solution Structure Of
      Human Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing

<400> SEQUENCE: 20

Xaa Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Pro Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 21
<211> LENGTH: 153
<212> TYPE: PRT
<213> ORGANISM: Artificial Sequence
<220> FEATURE:
<223> OTHER INFORMATION: Modifications of Chain A, Solution Structure Of
      Human Interleukin-1 Receptor Antagonist Protein
<220> FEATURE:
<221> NAME/KEY: (X1)= Xaa
<222> LOCATION: (2)..(2)
<223> OTHER INFORMATION: (X1) is Arg or Pro

<400> SEQUENCE: 21

Met Xaa Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45
```

```
Val Val Pro Ile Glu Pro His Ala Leu Phe Leu Gly Ile His Gly Gly
 50                  55                  60
Lys Met Cys Leu Ser Cys Val Lys Ser Gly Asp Glu Thr Arg Leu Gln
 65                  70                  75                  80
Leu Glu Ala Val Asn Ile Thr Asp Leu Ser Glu Asn Arg Lys Gln Asp
                 85                  90                  95
Lys Arg Phe Ala Phe Ile Arg Ser Asp Ser Gly Pro Thr Thr Ser Phe
            100                 105                 110
Glu Ser Ala Ala Cys Pro Gly Trp Phe Leu Cys Thr Ala Met Glu Ala
            115                 120                 125
Asp Gln Pro Val Ser Leu Thr Asn Met Pro Asp Glu Gly Val Met Val
130                 135                 140
Thr Lys Phe Tyr Phe Gln Glu Asp Glu
145                 150

<210> SEQ ID NO 22
<211> LENGTH: 153
<212> TYPE: PRT
<213> ORGANISM: Artificial Sequence
<220> FEATURE:
<223> OTHER INFORMATION: Modifications of either Chain A, Initial
      Crystallographic Analyses Of A Recombinant Interleukin-1 Receptor
      Antagonist Protein or Chain A, Solution Structure Of Human
      Interleukin-1 Receptor Antagonist Protein
<220> FEATURE:
<221> NAME/KEY: (X1)= Xaa
<222> LOCATION: (1)..(1)
<223> OTHER INFORMATION: (X1) is Met or nothing
<220> FEATURE:
<221> NAME/KEY: misc_feature
<222> LOCATION: (94)..(94)
<223> OTHER INFORMATION: Xaa can be any naturally occurring amino acid

<400> SEQUENCE: 22

Xaa Arg Pro Ser Gly Arg Lys Ser Ser Lys Met Gln Ala Phe Arg Ile
 1               5                  10                  15
Trp Asp Val Asn Gln Lys Thr Phe Tyr Leu Arg Asn Asn Gln Leu Val
                20                  25                  30
Ala Gly Tyr Leu Gln Gly Pro Asn Val Asn Leu Glu Glu Lys Ile Asp
            35                  40                  45
Val Val Pro Ile Glu Pro His Ala Leu Phe Leu Gly Ile His Gly Gly
 50                  55                  60
Lys Met Cys Leu Ser Cys Val Lys Ser Gly Asp Glu Thr Arg Leu Gln
 65                  70                  75                  80
Leu Glu Ala Val Asn Ile Thr Asp Leu Ser Glu Asn Arg Xaa Gln Asp
                 85                  90                  95
Lys Arg Phe Ala Phe Ile Arg Ser Asp Ser Gly Pro Thr Thr Ser Phe
            100                 105                 110
Glu Ser Ala Ala Cys Pro Gly Trp Phe Leu Cys Thr Ala Met Glu Ala
            115                 120                 125
Asp Gln Pro Val Ser Leu Thr Asn Met Pro Asp Glu Gly Val Met Val
130                 135                 140
Thr Lys Phe Tyr Phe Gln Glu Asp Glu
145                 150

<210> SEQ ID NO 23
<211> LENGTH: 159
<212> TYPE: PRT
<213> ORGANISM: Artificial Sequence
<220> FEATURE:
<223> OTHER INFORMATION: Modifications of interleukin 1 receptor
```

```
                      antagonist
<220> FEATURE:
<221> NAME/KEY: (X1)= Xaa
<222> LOCATION: (1)..(1)
<223> OTHER INFORMATION: (X1) is Cys or nothing
<220> FEATURE:
<221> NAME/KEY: (X2)= Xaa
<222> LOCATION: (2)..(2)
<223> OTHER INFORMATION: (X2) is Met or nothing
<220> FEATURE:
<221> NAME/KEY: (X3)= Xaa
<222> LOCATION: (3)..(3)
<223> OTHER INFORMATION: (X3) is Arg or Pro
<220> FEATURE:
<221> NAME/KEY: (X4)-(X7)= Xaa
<222> LOCATION: (7)..(88)
<223> OTHER INFORMATION: Each of (X4)-(X7) is a Cys or nothing
<220> FEATURE:
<221> NAME/KEY: (X8) = Xaa
<222> LOCATION: (122)..(122)
<223> OTHER INFORMATION: (X8) is Cys or Ser
<220> FEATURE:
<221> NAME/KEY: (X9) = Xaa
<222> LOCATION: (146)..(146)
<223> OTHER INFORMATION: (X9) is Cys or nothing

<400> SEQUENCE: 23

Xaa Xaa Xaa Pro Ser Gly Xaa Arg Lys Xaa Ser Xaa Ser Lys Met Gln
1               5                   10                  15

Ala Phe Arg Ile Trp Asp Val Asn Gln Lys Thr Phe Tyr Leu Arg Asn
                20                  25                  30

Asn Gln Leu Val Ala Gly Tyr Leu Gln Gly Pro Asn Val Asn Leu Glu
            35                  40                  45

Glu Lys Ile Asp Val Val Pro Ile Glu Pro His Ala Leu Phe Leu Gly
50                  55                  60

Ile His Gly Gly Lys Met Cys Leu Ser Cys Val Lys Ser Gly Asp Glu
65                  70                  75                  80

Thr Arg Leu Gln Leu Glu Ala Xaa Val Asn Ile Thr Asp Leu Ser Glu
                85                  90                  95

Asn Arg Lys Gln Asp Lys Arg Phe Ala Phe Ile Arg Ser Asp Ser Gly
            100                 105                 110

Pro Thr Thr Ser Phe Glu Ser Ala Ala Xaa Pro Gly Trp Phe Leu Cys
        115                 120                 125

Thr Ala Met Glu Ala Asp Gln Pro Val Ser Leu Thr Asn Met Pro Asp
130                 135                 140

Glu Xaa Gly Val Met Val Thr Lys Phe Tyr Phe Gln Glu Asp Glu
145                 150                 155

<210> SEQ ID NO 24
<211> LENGTH: 177
<212> TYPE: PRT
<213> ORGANISM: Homo sapiens

<400> SEQUENCE: 24

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
        50                  55                  60

Val Asn Leu Glu Glu Lys Ile Asp Val Val Pro Ile Glu Pro His Ala
```

```
                65                  70                  75                  80
Leu Phe Leu Gly Ile His Gly Gly Lys Met Cys Leu Ser Cys Val Lys
                    85                  90                  95

Ser Gly Asp Glu Thr Arg Leu Gln Leu Glu Ala Val Asn Ile Thr Asp
                100                 105                 110

Leu Ser Glu Asn Arg Lys Gln Asp Lys Arg Phe Ala Phe Ile Arg Ser
                115                 120                 125

Asp Ser Gly Pro Thr Thr Ser Phe Glu Ser Ala Ala Cys Pro Gly Trp
            130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 25
<211> LENGTH: 153
<212> TYPE: PRT
<213> ORGANISM: Artificial Sequence
<220> FEATURE:
<223> OTHER INFORMATION: Modification of sequence corresponding to amino
      acids 10-162 of interleukin-1 receptor antagonist protein isoform
      3 [Mus musculus]

<400> SEQUENCE: 25

Met Arg Pro Ser Gly Lys Arg Pro Cys Lys Met Gln Ala Phe Arg Ile
1               5                   10                  15

Trp Asp Thr Asn Gln Lys Thr Phe Tyr Leu Arg Asn Asn Gln Leu Ile
                20                  25                  30

Ala Gly Tyr Leu Gln Gly Pro Asn Ile Lys Leu Glu Glu Lys Ile Asp
            35                  40                  45

Met Val Pro Ile Asp Leu His Ser Val Phe Leu Gly Ile His Gly Gly
        50                  55                  60

Lys Leu Cys Leu Ser Cys Ala Lys Ser Gly Asp Asp Ile Lys Leu Gln
65                  70                  75                  80

Leu Glu Glu Val Asn Ile Thr Asp Leu Ser Lys Asn Lys Glu Glu Asp
                85                  90                  95

Lys Arg Phe Thr Phe Ile Arg Ser Glu Lys Gly Pro Thr Thr Ser Phe
                100                 105                 110

Glu Ser Ala Ala Cys Pro Gly Trp Phe Leu Cys Thr Thr Leu Glu Ala
            115                 120                 125

Asp Arg Pro Val Ser Leu Thr Asn Thr Pro Glu Glu Pro Leu Ile Val
        130                 135                 140

Thr Lys Phe Tyr Phe Gln Glu Asp Gln
145                 150

<210> SEQ ID NO 26
<211> LENGTH: 153
<212> TYPE: PRT
<213> ORGANISM: Homo sapiens

<400> SEQUENCE: 26

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
                20                  25                  30

Ala Gly Tyr Leu Gln Gly Pro Asn Val Asn Leu Glu Glu Lys Ile Asp
```

| | | 35 | | | 40 | | | | 45 | | |
|---|---|---|---|---|---|---|---|---|---|---|---|

Val Val Pro Ile Glu Pro His Ala Leu Phe Leu Gly Ile His Gly Gly
 50                          55                          60

Lys Met Cys Leu Ser Cys Val Lys Ser Gly Asp Glu Thr Arg Leu Gln
65                       70                          75                      80

Leu Glu Ala Val Asn Ile Thr Asp Leu Ser Asn Arg Lys Gln Asp
                        85                          90                           95

Lys Arg Phe Ala Phe Ile Arg Ser Asp Ser Gly Pro Thr Thr Ser Phe
                100                         105                         110

Glu Ser Ala Ala Cys Pro Gly Trp Phe Leu Cys Thr Ala Met Glu Ala
                115                         120                         125

Asp Gln Pro Val Ser Leu Thr Asn Met Pro Asp Glu Gly Val Met Val
                130                         135                         140

Thr Lys Phe Tyr Phe Gln Glu Asp Glu
145                         150

```
<210> SEQ ID NO 27
<211> LENGTH: 1707
<212> TYPE: DNA
<213> ORGANISM: Homo sapiens

<400> SEQUENCE: 27
ggaagacctc ctgtcctatc aggccctccc catggcttta gagacgatct gccgaccctc    60
tgggagaaaa tccagcaaga tgcaagcctt cagaatctgg gatgttaacc agaagacctt   120
ctatctgagg aacaaccaac tagttgccgg atacttgcaa ggaccaaatg tcaatttaga   180
agaaaagata gatgtggtac ccattgagcc tcatgctctg ttcttgggaa tccatggagg   240
gaagatgtgc ctgtcctgtg tcaagtctgg tgatgagacc agactccagc tggaggcagt   300
taacatcact gacctgagcg agaacagaaa gcaggacaag cgcttcgcct tcatccgctc   360
agacagtggc cccaccacca gttttgagtc tgccgcctgc cccggttggt tcctctgcac   420
agcgatggaa gctgaccagc ccgtcagcct caccaatatg cctgacgaag cgtcatggt   480
caccaaattc tacttccagg aggacgagta gtactgccca ggcctgcctg ttcccattct   540
tgcatggcaa ggactgcagg gactgccagt ccccctgccc cagggctccc ggctatgggg   600
gcactgagga ccagccattg aggggtggac cctcagaagg cgtcacaaca acctggtcac   660
aggactctgc ctcctcttca actgaccagc ctccatgctg cctccagaat ggtctttcta   720
atgtgtgaat cagagcacag cagccctgc acaaagccct tccatgtcgc ctctgcattc     780
aggatcaaac cccgaccacc tgcccaacct gctctcctct tgccactgcc tcttcctccc   840
tcattccacc ttcccatgcc ctggatccat caggccactt gatgaccccc aaccaagtgg   900
ctcccacacc ctgttttaca aaaagaaaa gaccagtcca tgagggaggt ttttaagggt     960
ttgtggaaaa tgaaaattag gatttcatga tttttttttt tcagtccccg tgaaggagag   1020
cccttcattt ggagattatg ttctttcggg gagaggctga ggacttaaaa tattcctgca   1080
tttgtgaaat gatggtgaaa gtaagtggta gcttttccct tctttttctt ctttttttgt   1140
gatgtcccaa cttgtaaaaa ttaaaagtta tggtactatg ttagccccat aattttttt    1200
ttccttttaa aacacttcca taatctggac tcctctgtcc aggcactgct gcccagcctc   1260
caagctccat ctccactcca gattttttac agctgcctgc agtactttac ctcctatcag   1320
aagtttctca gctcccaagg ctctgagcaa atgtggctcc tggggttct ttcttcctct    1380
gctgaaggaa taaattgctc cttgacattg tagagcttct ggcacttgga gacttgtatg   1440
```

-continued

| | | | | | |
|---|---|---|---|---|---|
| aaagatggct | gtgcctctgc | ctgtctcccc | caccaggctg | ggagctctgc | agagcaggaa 1500 |
| acatgactcg | tatatgtctc | aggtccctgc | agggccaagc | acctagcctc | gctcttggca 1560 |
| ggtactcagc | gaatgaatgc | tgtatatgtt | gggtgcaaag | ttccctactt | cctgtgactt 1620 |
| cagctctgtt | ttacaataaa | atcttgaaaa | tgcctaaaaa | aaaaaaaaaa | aaaaaaaaaa 1680 |
| aaaaaaaaaa | aaaaaaaaaa | aaaaaaa | | | 1707 |